United States Patent

Nakagawa et al.

[11] 4,147,869
[45] Apr. 3, 1979

[54] 3,4-DIHYDROCARBOSTYRIL DERIVATIVES AND PROCESS FOR PREPARING THE SAME

[75] Inventors: Kazuyuki Nakagawa; Yasuo Oshiro, both of Tokushima, Japan

[73] Assignee: Otsuka Pharmaceutical Co., Ltd., Tokyo, Japan

[21] Appl. No.: 795,042

[22] Filed: May 9, 1977

[30] Foreign Application Priority Data

May 8, 1976 [JP] Japan .................................. 51-52588
Feb. 25, 1977 [JP] Japan .................................. 52-20692

[51] Int. Cl.² .................. C07D 401/12; C07D 315/38; C07D 315/40
[52] U.S. Cl. .................................... 544/363; 424/258; 544/128; 546/158
[58] Field of Search ..... 260/268 BQ, 288 R, 288 CE; 544/363, 128

[56] References Cited

U.S. PATENT DOCUMENTS 3,910,924 10/1975 Tamura et al. .................. 260/286 R
3,953,456 4/1976 Nakagawa et al. .................. 424/258
3,975,391 8/1976 Nakagawa et al. .................. 424/258

*Primary Examiner*—Paul M. Coughlan, Jr.
*Attorney, Agent, or Firm*—Sughrue, Rothwell, Mion, Zinn and Macpeak

[57] ABSTRACT

3,4-Dihydrocarbostyril derivatives represented by the formula (I)

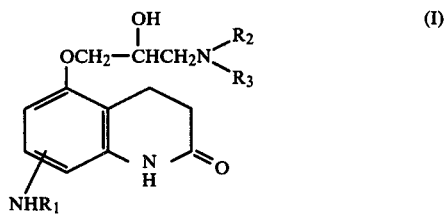

wherein $R_1$ represents an alkylcarbonyl group, a cycloalkylcarbonyl group, an alkylsulfonyl group, a phenylsulfonyl group, a carbamoyl group or an alkoxycarbonyl group, $R_2$ and $R_3$, which may be the same or different, each represents a hydrogen atom, an alkyl group, a phenylalkyl group or a phenoxyalkyl group, or $R_2$ and $R_3$ can form, when taken together with the nitrogen atom to which they are attached, a heterocyclic group selected from the group consisting of piperidino, pyrrolidino, morpholino and 1-piperazinyl which may be substituted with a phenyl group or an alkyl group having 1 to 4 carbon atoms, with the proviso that, when the group $-NHR_1$ is attached to the 8-position of the 3,4-dihydrocarbostyril nucleus in which $R_1$ represents an alkylcarbonyl group and one of $R_2$ and $R_3$ represents a hydrogen atom, then the other group of $R_2$ and $R_3$ cannot be an alkyl group, pharmaceutically acceptable acid addition salts thereof, and process for preparing the same.

7 Claims, No Drawings

3,4-DIHYDROCARBOSTYRIL DERIVATIVES AND PROCESS FOR PREPARING THE SAME

BACKGROUND OF THE INVENTION

1. Field of the Invention

This invention relates to 3,4-dihydrocarbostyril derivatives and a process for preparing the same. More particularly, this invention relates to 3,4-dihydrocarbostyril derivatives represented by the formula (I) hereinafter described, the pharmaceutically acceptable acid addition salts thereof, and a process for preparing the 3,4-dihydrocarbostyril derivatives of the formula (I).

2. Description of the Prior Art

It is well known that certain carbostyril derivatives exhibit useful pharmaceutical activities. Representative compounds of this type have been disclosed in Journal of Medical Chemistry, Vol. 15, No. 3, pp 260–266 (1972), Japanese Patent Publication No. 38789/1971 and Chemical Abstracts, 62, 16212e (1965), etc. However, these prior art references do not teach that the compounds having a wide variety of substituted-amino groups at the 6-, 7- or 8-position of the 3,4-dihydrocarbostyril moiety possess an excellent β-adrenoreceptor blocking activity.

Hitherto, various carbostyril compounds have been disclosed as having a β-adrenoreceptor blocking activity. For example, U.S. Pat. Nos. 3,340,266, 3,910,924 and 3,953,456, and German Patent Application DT 2,549,889 disclose that 3,4-dihydrocarbostyril derivatives having a (2-hydroxy-3-substituted-amino)propoxy group at the 5-, 6-, 7- or 8-position of the 3,4-dihydrocarbostyril nucleus possess a β-adrenoreceptor blocking activity, i.e., β-blockers. Also, Japanese Patent Application Laid Open to Public Inspection Nos. 48676/1976 (published on Apr. 26, 1976) and 52177/1976 (published on May 8, 1976) disclose 3,4-dihydrocarbostyril compounds having a (2-hydroxy-3-substituted-amino)propoxy group at the 5-position and a nitro group, an acetamido group or an amino group at the 8-position useful as β-blockers.

However, these β-blockers are usually contraindication to subject suffering from bronchial asthma and, therefore, it has been desired to develope β-blockers having a high cardioselectivity.

Recently, carbostyril compounds having a (2-hydroxy-3-substituted-amino)propoxy group at the 5-position of the carbostyril or 3,4-dihydrocarbostyril nucleus were found to have a cardioselective β-adrenoreceptor blocking activity, as disclosed in German Patent Application No. DT 2,615,406 and U.S. application Ser. No. 778,539 filed on Mar. 17, 1977 (German Patent Application No. P27 11 719.7 filed on Mar. 17, 1977). Such cardioselective β-blockers would be very useful for treatment of carbiac disorders such as angina pectoris, heart arrhythmia and hypertension. The compounds of the present invention were also found to have excellent cardioselectivity better than that of these known compounds and are useful in treatment or prophylaxis of cardiac disorders in subjects suffering also from chronic obstructive lung disease such as bronchial asthma.

DETAILED DESCRIPTION OF THE INVENTION

As a result of extensive studies, it was found that the 3,4-dihydrocarbostyril derivatives having the formula (I) above and the pharmaceutically acceptable acid addition salts thereof possess an excellent cardioselective β-blocking activity.

The present invention therefore provides a 3,4-dihydrocarbostyril derivative represented by the formula (I)

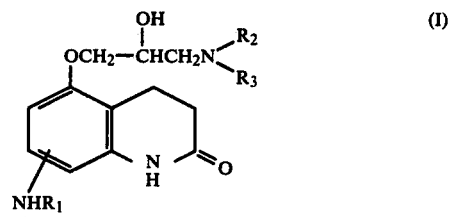

wherein $R_1$ represents an alkylcarbonyl group, a cycloalkylcarbonyl group, an alkylsulfonyl group, a phenylsulfonyl group, a carbamoyl group or an alkoxycarbonyl group, $R_2$ and $R_3$, which may be the same or different, each represents a hydrogen atom, an alkyl group, a phenylalkyl group or a phenoxyalkyl group, or $R_2$ and $R_3$ can form, when taken together with the nitrogen atom to which they are attached, a heterocyclic group selected from the group consisting of piperidino, pyrrolidino, morpholino and 1-piperazinyl which may be substituted with a phenyl group or an alkyl group having 1 to 4 carbon atoms, with the proviso that, when the group -$NHR_1$ is attached to the 8-position of the 3,4-dihydrocarbostyril nucleus in which $R_1$ represents an alkylcarbonyl group and one of $R_2$ and $R_3$ represents a hydrogen atom, then the other group of $R_2$ and $R_3$ cannot be an alkyl group, and the pharmaceutically acceptable acid addition salts thereof, which are useful as cardioselective β-blockers.

The present invention also provides a process for preparing a 3,4-dihydrocarbostyril derivative represented by the formula (I)

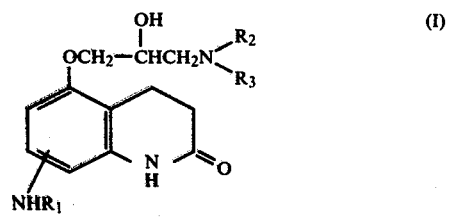

wherein $R_1$, $R_2$ and $R_3$ are as defined above, which comprises reacting a 3,4-dihydrocarbostyril compound of the formula (II)

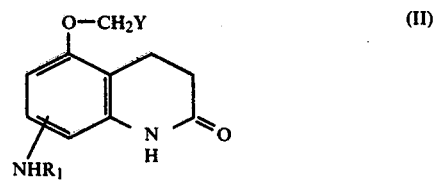

wherein $R_1$ as defined above, and Y represents a

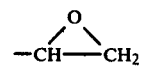

group or a

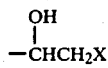

group wherein X represents a halogen atom, with an amine compound of the formula (III)

wherein $R_2$ and $R_3$ are as defined above, at a temperature of about 0° to about 100° C.

The term "alkylcarbonyl" as used herein means an alkylcarbonyl group having a straight or branched chain alkyl group of 1 to 6 carbon atoms in the alkyl moiety thereof which may be substituted with halogen atoms and includes, for example, acetyl, trifluoroacetyl, propionyl, pentafluoropropionyl, butyryl, isobutyryl, valeryl, isovaleryl, pivaloyl and the like.

The term "cycloalkylcarbonyl" as used herein means a cycloalkylcarbonyl group having a cycloalkyl group of 3 to 7 carbon atoms in the cycloalkyl moiety thereof and includes, for example, cyclopropylcarbonyl, cyclobutylcarbonyl, cyclopentylcarbonyl, cyclohexylcarbonyl, cycloheptylcarbonyl and the like.

The term "alkylsulfonyl" as used herein means an alkylsulfonyl group having a straight or branched chain alkyl group of 1 to 4 carbon atoms in the alkyl moiety and includes, for example, methylsulfonyl, ethylsulfonyl, propylsulfonyl, isopropylsulfonyl, n-butylsulfonyl, tert-butylsulfonyl and the like.

The term "carbamoyl" as used herein means a carbamoyl group which may be substituted on the nitrogen atom thereof with an alkyl group having 1 to 6 carbon atoms and includes, for example, carbamoyl, N-methylcarbamoyl, N-ethylcarbamoyl, N-isopropylcarbamoyl, N-butylcarbamoyl, N,N-diethylcarbamoyl, N-ethyl-N-methylcarbamoyl and the like.

The term "alkoxycarbonyl" as used herein means an alkoxycarbonyl group containing a straight or branched chain alkoxy group having 1 to 4 carbon atoms attached to a carbonyl group and includes, for example, methoxycarbonyl, ethoxycarbonyl, propoxycarbonyl, isopropoxycarbonyl, butoxycarbonyl, tert-butoxycarbonyl and the like.

The term "alkyl" as used herein means a straight or branched chain alkyl group having 1 to 4 carbon atoms and includes, for example, methyl, ethyl, propyl, isopropyl, butyl, sec-butyl, tert-butyl and the like.

The term "phenylalkyl" as used herein means a phenylalkyl group having a straight or branched chain alkylene group having 1 to 6 carbon atoms in the alkyl moiety and includes, for example, benzyl, 2-phenylethyl, 1-phenylethyl, 2-methyl-2-phenylpropyl, 4-phenylbutyl, 6-phenylhexyl, 1,1-dimethyl-2-phenylethyl, 2-methyl-4-phenylbutyl, 2-methyl-3-phenylpropyl and the like.

The term "phenoxyalkyl" as used herein means a phenoxyalkyl group having a straight or branched chain alkylene group of 1 to 6 carbon atoms in the alkyl moiety thereof and includes, for example, phenoxymethyl, 2-phenoxyethyl, 1-phenoxyethyl, 2-methyl-2-phenoxypropyl, 4-phenoxybutyl, 6-phenoxyhexyl, 1,1-dimethyl-2-phenoxyethyl, 2-methyl-4-phenoxybutyl, 2-methyl-3-phenoxypropyl and the like.

The above phenyl, phenylsulfonyl, phenylalkyl and phenoxyalkyl groups may contain 1 to 3 substituents which may be the same or different. Examples of such substituents include an alkyl group having 1 to 3 carbon atoms such as methyl, ethyl, propyl, isopropyl, and the like, an alkoxy group having 1 to 3 carbon atoms such as methoxy, ethoxy, propoxy, isopropoxy and the like, an alkylenedioxy group having 1 to 2 carbon atoms such as methylenedioxy or ethylenedioxy and the like, a halogen atom such as a chlorine, bromine, iodine or fluorine atom, or a carbamoyl group.

Typical examples of groups having the above substituents are, for example, 4-methoxyphenyl, 2-methoxyphenyl, 3-ethoxyphenyl, 3,4-dimethoxyphenyl, 3,5-dimethoxyphenyl, 3,4-methylenedioxyphenyl, 3,4,5-trimethoxyphenyl, 4-chlorophenyl, 4-fluorophenyl, 2-chlorophenyl, 3-bromophenyl, 3,4-dichlorophenyl, 2-methylphenyl, 3-propylphenyl, 4-methylphenyl, p-toluenesulfonyl, 3,4-dimethoxyphenylsulfonyl, 4-chlorophenylsulfonyl, 3,4-dichlorophenylsulfonyl, 2-fluorophenylsulfonyl, 2-(3,4-dimethoxyphenyl)ethyl, 2-(4-fluorophenyl)ethyl, 2-(3,4-dichlorophenyl)ethyl, 2-(3,4,5-trimethoxyphenyl)ethyl, 4-(3,4-dimethoxyphenyl)butyl, 2-(3,4-methylenedioxyphenyl)ethyl, 3-(3,5-dimethoxyphenyl)propyl, 2-(4-carbamoylphenyl)ethyl, 2-(4-chloro-3,5-dimethoxyphenyl)ethyl, 2-(2-isopropoxyphenyl)ethyl, 2-(4-methoxyphenyl)ethyl, 1,1-dimethyl-2-(3,4-dimethoxyphenyl)ethyl, 2-(3,4-dimethoxyphenoxy)ethyl, 2-(3,5-dimethoxyphenoxy)ethyl, 2-(3,4-ethylenedioxyphenoxy)ethyl, 2-(4-fluorophenoxy)ethyl, 2-(3,4-dichlorophenoxy)ethyl, 2-(4-carbamoylphenoxy)ethyl, 2-(4-chloro-3,5-dimethoxyphenoxy)ethyl, 2-(4-methoxyphenoxy)ethyl, 4-(4-methoxyphenoxy)butyl, 1,1-dimethyl-2-(3,4-dimethoxyphenoxy)ethyl and the like.

The term "pharmaceutically acceptable acid addition salts" as used herein means those formed with pharmaceutically acceptable inorganic and organic acids which are well known in the art such as, for example, hydrochloric acid, sulfuric acid, phosphoric acid, hydrobromic acid, acetic acid, lactic acid, oxalic acid, malonic acid, succinic acid, maleic acid, tartaric acid, fumaric acid, malic acid, mandelic acid, methanesulfonic acid, benzoic acid and the like.

The 3,4-dihydrocarbostyril derivatives represented by the formula (I) can be prepared by reacting a 3,4-dihydrocarbostyril compound of the formula (II), i.e., a 2,3-epoxypropoxy-3,4-dihydrocarbostyril compound of the formula (IIa) or a 2-hydroxy-3-halopropoxy-3,4-dihydrocarbostyril compound of the formula (IIb), with an amine compound of the formula (III), as illustrated by the following reaction scheme:

Reaction Scheme 1

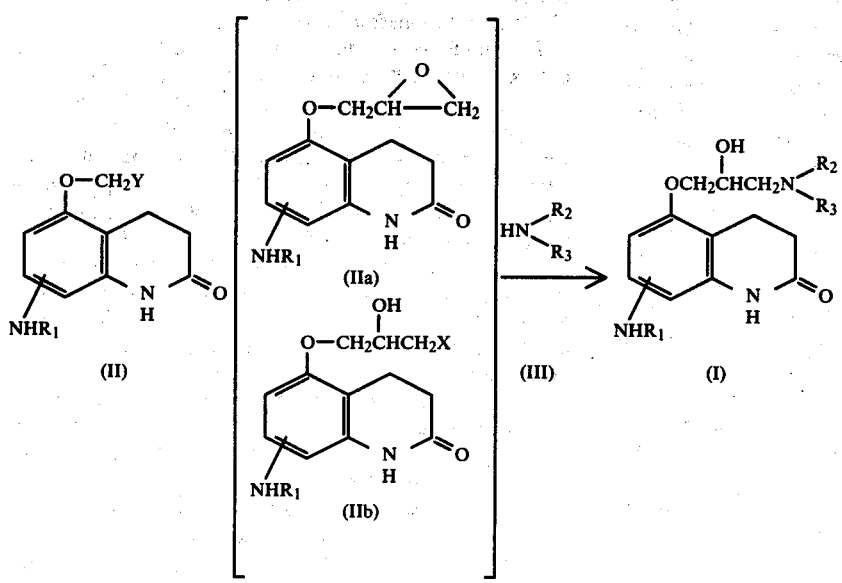

wherein $R_1$, $R_2$ and $R_3$ are as defined above, and Y represents a

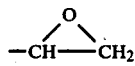

group or a

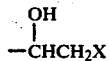

group wherein X represents a halogen atom.

More specifically, the starting material, 3,4-dihydrocarbostyril compounds of the formula (II), can be either an epoxy form having the formula (IIa), a 2-hydroxy-3-halopropoxy form having the formula (IIb) or a mixture thereof.

The reaction between a 2,3-epoxypropoxy-3,4-dihydrocarbostyril compound of the formula (IIa) and an amine of the formula (III) can be carried out in the absence of solvents, but is preferably conducted in the presence of a solvent, for example, ethers such as diethyl ether, dioxane, tetrahydrofuran and the like, aromatic hydrocarbons such as benzene, toluene, xylene and the like, lower alcohols such as methanol, ethanol, isopropanol and the like, ketones such as acetone, methyl ethyl ketone and the like, water, acetonitrile, dimethyl sulfoxide, dimethylformamide, etc., more preferably in an alcohol such as methanol, ethanol, isopropanol and the like.

The reaction can be carried out at a temperature of about 0° C. to 100° C., preferably 0° C. to 70° C., using an approximately equimolar amount to a molar excess, preferably 3 to 8 mols, of the amine of the formula (III) per mol of the 2,3-epoxypropoxy-3,4-dihydrocarbostyril compound of the formula (IIa).

The reaction between a 2-hydroxy-3-halopropoxy-3,4-dihydrocarbostyril of the formula (IIb) and an amine of the formula (III) can be advantageously carried out in the presence of a base, for example, sodium hydroxide, potassium hydroxide, sodium carbonate, potassium carbonate and the like, preferably sodium carbonate or potassium carbonate, but the reaction can be carried out in the absence of such base.

The reaction can be carried out at a temperature of about 0° to about 100° C., preferably 50° to 80° C., in the presence or absence of solvents, but advantageously carried out in the presence of solvents, e.g., ethers such as diethyl ether, dioxane, tetrahydrofuran and the like, aromatic hydrocarbons such as benzene, toluene, xylene and the like, lower alcohols such as methanol, ethanol, propanol, isopropanol and the like, ketones such as acetone, methyl ethyl ketone and the like, water, dimethyl sulfoxide, dimethylformamide, etc., preferably lower alcohols such as methanol, ethanol, isopropanol and the like.

In the above reaction, the amine of the formula (III) is used in a molar excess, preferably 3 to 8 mols, per mol of the 2-hydroxy-3-halopropoxy-3,4-dihydrocarbostyril compound of the formula (IIb).

The reaction between a mixture of the 3,4-dihydrocarbostyril compounds of the formulae (IIa) and (IIb) and an amine compound of the formula (III) can be carried out in the presence or absence of the base as set forth above at a temperature of about 0° C. to about 100° C., preferably 50° to 80° C. The type of solvents and the amount of the amine of the formula (III) which can be used in this reaction are the same as those set forth above for the reaction of the compound of the formula (IIa) or (IIb) with the amine of the formula (III).

The time required for completing the reaction of the 3,4-dihydrocarbostyril compound of the formula (IIa), (IIb) or a mixture thereof with an amine varies depending upon the temperature used, but is generally about 0.5 to about 30 hours, more generally, 2 to 14 hours.

Representative amines of the formula (III) are, for example, methylamine, ethylamine, propylamine, isopropylamine, tert-butylamine and the like, phenethylamine, 3,4-dimethoxyphenethylamine, 3,4-methylenedioxyphenethylamine, 2-(4-methoxyphenoxy)ethylamine, 2-(4-carbamoylphenoxy)ethylamine, 3,4,5-trimethoxyphenethylamine, benzylisopropylamine, N-benzyl-N-[2-(4-carbamoylphenoxy)ethyl]amine, 1-methyl-2-phenoxyethylamine, phenylpiperazine, m-chlorophenylpiperazine, p-methoxyphenylpiperazine, o-methoxyphenylpiperazine, o-tolylpiperazine, m-methoxyphenylpiperazine, m-tolylpiperazine, o-chlorophenylpiperazine, p-chlorophenylpiperazine, p-tolylpiperazine, o-ethylphenylpiperazine, p-bromophenylpiperazine, o-styrylpiperazine, p-iodophenylpiperazine, p-ethoxyphenylpiperazine, m-propyloxyphenylpiperazine, p-propylphenylpiperazine, piperidine, pyrrolidine, morpholine and the like.

The starting material of the formula (II) are novel compounds and can be derived from the corresponding known nitro-3,4-dihydrocarbostyril compounds of the formula (IV) as disclosed in Japanese Patent Application Laid Open to Public Inspection No. 6971/1976 (published on Jan. 20, 1976) via various steps.

That is, the starting materials having the formula (II) can be prepared by reducing a nitro-substituted 3,4-dihydrocarbostyril of the formula (VII) according the procedure disclosed in Japanese Patent Application Laid Open to Public Inspection No. 6972/1976 (published on Jan. 20, 1976) to obtain a corresponding amino-substututed-3,4-dihydrocarbostyril of the formula (IV), then subjecting the resulting amino-substituted-3,4-dihydrocarbostyril of the formula (IV) to acylation, alkanesulfonation, allenesulfonation, carbamoylation or alkoxycarbonization in a conventional manner, depending upon the type of the desired substituent $R_1$, to obtain a 3,4-dihydrocarbostyril compound of the formula (V), and reacting the resulting compound of the formula (V) with an epihalohydrin of the formula (VI), as illustrated by the following Reaction Scheme 2 below.

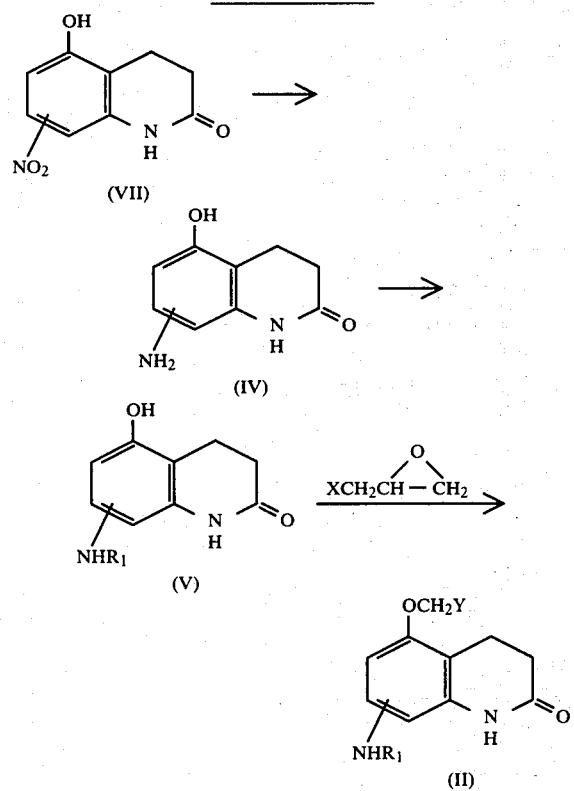

Reaction Scheme 2 wherein $R_1$, Y and X are as defined above.

The processes for preparing the starting compound of the formula (II) of the present invention are further illustrated hereinafter in greater detail.

The reduction of the compound of the formula (VII) can be carried out using a conventional reducing agent, for example, a combination of stannous chloride and hydrochloric acid, at a temperature of about 0° to about 150° C., or by hydrogenation in the presence of a conventional hydrogenating catalyst, for example, palladium black, palladium-carbon, Raney nickel, platinum oxide, at a temperature of about 0° to about 100° C.

The resulting amino-substituted-3,4-dihydrocarbostyril of the formula (IV) is then subjected to the above-described reaction. The acylation, carbamoylation and alkoxycarbonylation can be effected using an acid halide or acid anhydride, and the alkylsulfonylation and phenylsulfonylation can be effected using as a sulfonylation agent a sulfonic acid halide of the formula $RSO_2X$ wherein R represents an alkyl group or a phenyl group and X is as defined above.

The above reaction can be carried out in the presence of a base, for example, an inorganic base such as sodium, potassium, sodium hydroxide, potassium hydroxide, sodium carbonate, potassium carbonate, sodium bicarbonate, potassium bicarbonate, potassium acetate, sodium acetate, ammonium acetate and the like, or an organic base such as pyridine, trimethylamine, triethylamine, N,N-dimethylaniline and the like in the presence or absence of a solvent, preferably in the presence of a solvent, at a temperature of above 0° to about 200° C., preferably 10° to 100° C.

Suitable solvents which can be used in the above-described reaction are water, lower alcohols such as methanol, ethanol, isopropanol and the like, ethers such as diethyl ether, dioxane, tetrahydrofuran and the like, aromatic hydrocarbons such as benzene, toluene, xylene and the like, ketones such as acetone, methyl ethyl ketone and the like, esters such as ethyl acetate and the like, organic carboxylic acids such as acetic acid, butyric acid and the like. Alternatively, the above-described organic base, e.g., pyridine, can be used as a solvent.

The acid halide, acid anhydride or sulfonic acid halide can be used in an amount of an approximately equimolar to about 5 mols, preferably 1 to 1.5 mol, per mol of the compound of the formula (IV).

The reaction between the compound of the formula (V) and an epihalohydrin of the formula (VI) can be carried out in the presence of a base at a temperature of about 0° to about 150° C., preferably 50° to 100° C., in the absence or, preferably, in the presence of a solvent.

Suitable examples of bases which can be used in the above reaction are inorganic bases, for example, alkali metal hydroxides such as sodium hydroxide, potassium hydroxide and the like alkali metal carbonates such as sodium carbonate, potassium carbonate and the like, alkali metal alkoxides such as sodium ethoxide, sodium methoxide and the like, alkali metal hydrides such as sodium hydride and the like, alkali metals such as sodium, potassium and the like, or organic bases such as pyridine, piperidine, triethylamine and the like.

Suitable examples of solvents which can be used in the above reaction are lower alcohols such as methanol, ethanol, isopropanol and the like, ketones such as acetone, methyl ethyl ketone and the like, ethers such as diethyl ether, dioxane and the like, and aromatic hydrocarbons such as benzene, toluene, xylene and the like, preferably lower alcohols such as methanol, ethanol, isopropanol and the like.

The epihalohydrin of the formula (VI) can be epichlorohydrin, epibromohydrin or epiiodohydrin and can be used in an approximately equimolar amount to a molar excess amount, preferably 5 to 10 mols, per mol of the compound of the formula (V).

In the above reaction, the hydroxyl group attached to the 5-position of the compounds of the formula (V) is converted into a (2,3-epoxy)propoxy group or a 3-halo-2-hydroxypropoxy group and the resulting reaction product of the formula (II) is usually a mixture of corresponding 5-(2,3-epoxy)propoxy compound and 5-(3-halo-2-hydroxypropoxy) compound. The mixture per se thus obtained is usually used for the subsequent reaction with an amine of the formula (III) without isolating each of the compounds, but, if desired, each of the compounds can be isolated and purified by conventional procedures, for example, by fractional crystallization, column chromatography and then reacted with an amine of the formula (III).

The present invention includes, in its scope, pharmaceutically acceptable acid addition salts as described previously as well as optical isomers of the 3,4-dihydrocarbostyril compounds of the formula (I).

As is apparent to one skilled in the art, the 3,4-dihydrocarbostyril compounds of the formula (I) can be prepared through various routes. Representative routes which can be used are shown in Reaction Scheme 3 below.

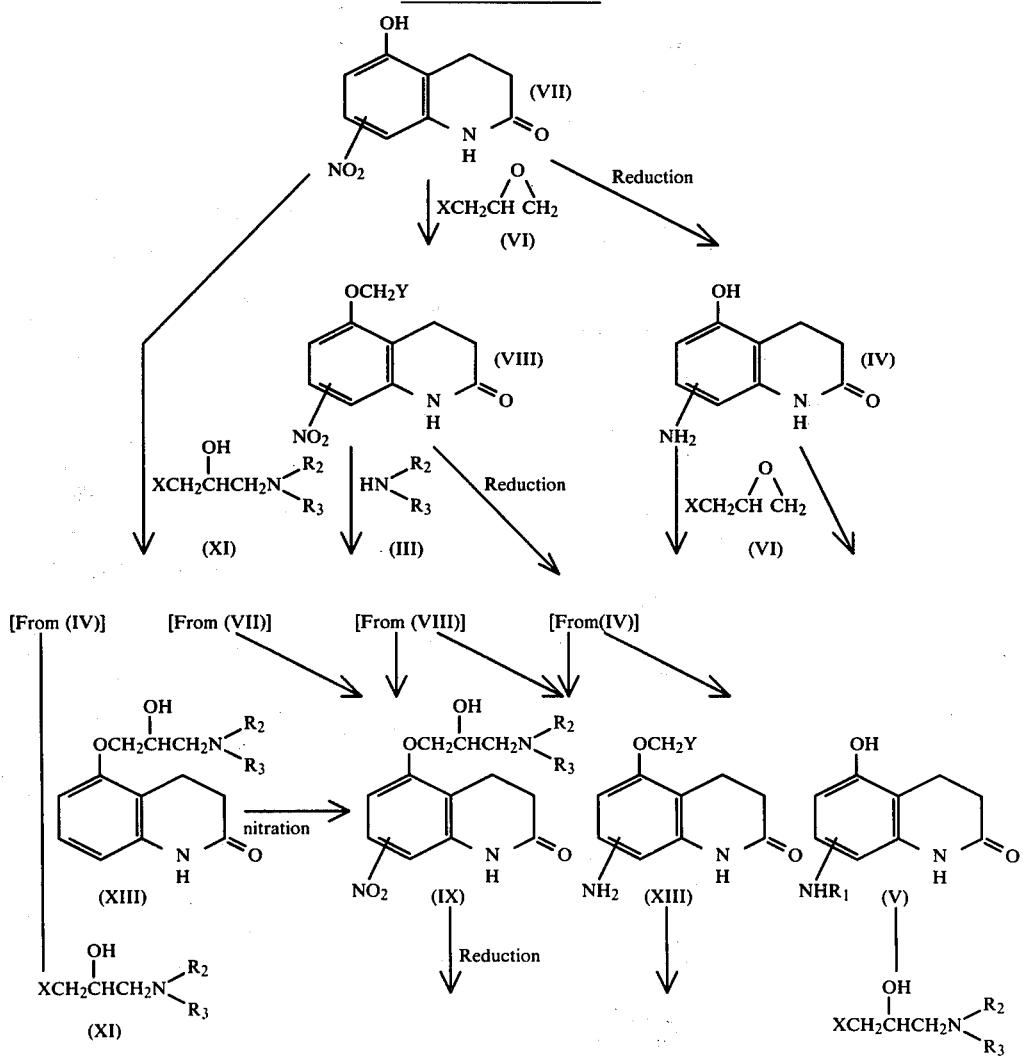

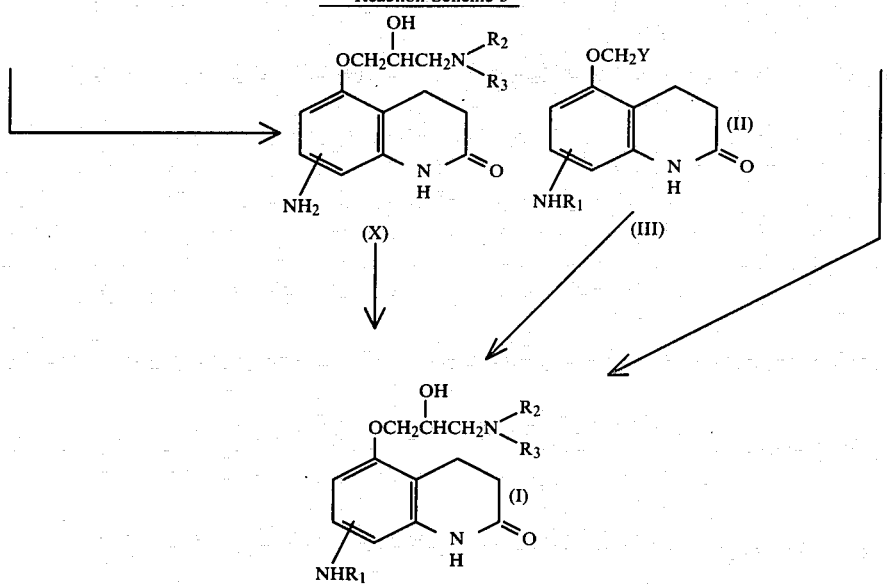

Representative compounds of the present invention having the formula (I) are:

8-acetylamino-5-(3-amino-2-hydroxy)propoxy-3,4-dihydrocarbostyril,
8-acetylamino-5-[3-(3,4-dimethoxyphenetylamino)-2-hydroxy]-propoxy-3,4-dihydrocarbostyril,
8-butyrylamino-5-[3-(4-carbamoylphenoxyethylamino)-2-hydroxy]propoxy-3,4-dihydrocarbostyril,
8-isobutyrylamino-5-[3-(3,4-methylenedioxyphenethylamino)2-hydroxy]propoxy-3,4-dihydrocarbostyril,
8-acetylamino-5-[3-(4-phenylbutylamino)-2-hydroxy]-propoxy-3,4-dihydrocarbostyril,
8-acetylamino-5-[3-(3,4,5-trimethoxyphenethylamino)-2-hydroxy]propoxy-3,4-dihydrocarbostyril,
8-acetylamino-5-[2-hydroxy-3-(4-o-methoxyphenyl-1-piperazinyl)]propoxy-3,4-dihydrocarbostyril,
8-acetylamino-5-[2-hydroxy-3-(3,5-dimethoxyphenethylamino)]propoxy-3,4-dihydrocarbostyril,
8-acetylamino-5-[2-hydroxy-3-(4-p-methoxyphenyl-1-piperazinyl)]propoxy-3,4-dihydrocarbostyril,
8-propionylamino-5-[2-hydroxy-3-(4-m-tolyl-1-piperazinyl)]propoxy-3,4-dihydrocarbostyril,
8-isobutyrylamino-5-[2-hydroxy-3-(4-p-methoxyphenyl-1-piperazinyl)]propoxy-3,4-dihydrocarbostyril,
8-acetylamino-5-[2-hydroxy-3-(4-p-bromophenyl-1-piperazinyl)]propoxy-3,4-dihydrocarbostyril,
8-valerylamino-5-[2-hydroxy-3-(4-p-propoxyphenyl-1-piperazinyl)]propoxy-3,4-dihydrocarbostyril,
8-trifluoroacetylamino-5-(3-tert-butylamino-2-hydroxy)propoxy-3,4-dihydrocarbostyril,
8-trifluoroacetylamino-5-[3-(3,4-dimethoxyphenethylamino)2-hydroxy]propoxy-3,4-dihydrocarbostyril,
8-trifluoroacetylamino-5-[3-(4-methoxyphenoxyethylamino)2-hydroxy]propoxy-3,4-dihydrocarbostyril,
7-acetylamino-5-[3-(3,4-dimethoxyphenethylamino)-2-hydroxy]propoxy-3,4-dihydrocarbostyril,
7-propionylamino-5-(3-tert-butylamino-2-hydroxy)-propoxy-3,4-dihydrocarbostyril,
8-acetylamino-5-[2-hydroxy-3-(3,5-dimethoxyphenoxyethylamino)]propoxy-3,4-dihydrocarbostyril,
8-acetylamino-5-{3-[1,1-dimethyl-2-(3,4-dimethoxyphenyl)ethylamino]-2-hydroxy}propoxy-3,4-dihydrocarbostyril,
6-acetylamino-5-(2-hydroxy-3-isopropylamino)-propoxy-3,4-dihydrocarbostyril,
6-propionylamino-5-[3-(3,4-dimethoxyphenethylamino)-2-hydroxy]propoxy-3,4-dihydrocarbostyril,
6-trifluoroacetylamino-5-(2-hydroxy-3-isopropylamino)propoxy-3,4-dihydrocarbostyril,
6-trifluoroacetylamino-5-[3-(4-methoxyphenoxyethylamino)2-hydroxy]propoxy-3,4-dihydrocarbostyril,
6-butyrylamino-5-[2-hydroxy-3-(4-p-methoxyphenyl-1-piperazinyl)]propoxy-3,4-dihydrocarbostyril,
8-cyclohexylcarbonylamino-5-]2-hydroxy-3-(3,5-dimethoxyphenethylamino)]propoxy-3,4-dihydrocarbostyril,
8-cyclopentylcarbonylamino-5-(2-hydroxy-3-isopropylamino)propoxy-3,4-dihydrocarbostyril,
8-cyclohexylcarbonylamino-5-(3-tert-butylamino-2-hydroxy)propoxy-3,4-dihydrocarbostyril,
8-cyclohexylcarbonylamino-5-[3-(3,4-dimethoxyphenethylamino)2-hydroxy]propoxy-3,4-dihydrocarbostyril,
8-cyclohexylcarbonylamino-5-[2-hydroxy-3-(4-methoxyphenoxyethylamino)]propoxy-3,4-dihydrocarbostyril,
8-cyclohexylcarbonylamino-5-{3-[1,1-dimethyl-2-(3,4-dimethoxyphenyl)ethylamino]-2-hydroxy}propoxy-3,4-dihydrocarbostyril,
8-cycloheptylcarbonylamino-5-(2-hydroxy-3-phenethylamino)propoxy-3,4-dihydrocarbostyril,
8-cyclohexylcarbonylamino-5-[2-hydroxy-3-(4-phenyl-1-piperazinyl)]propoxy-3,4-dihydrocarbostyril,
8-cyclohexylcarbonylamino-5-[2-hydroxy-3-(4-o-tolyl-1-piperazinyl)]propoxy-3,4-dihydrocarbostyril,
7-cyclohexylcarbonylamino-5-(3-tert-butylamino-2-hydroxy)propoxy-3,4-dihydrocarbostyril,
7-cyclohexylcarbonylamino-5-[3-(3,4-dimethoxyphenethylamino)2-hydroxy]propoxy-3,4-dihydrocarbostyril, 7-cyclohexylcarbonylamino-5-[3-(4-methoxyphenoxyethylamino)2-hydroxy]propoxy-3,4-dihydrocarbostyril,
6-cyclohexylcarbonylamino-5-[3-(1-methylbenzylamino)-2-hydroxy]propoxy-3,4-dihydrocarbostyril,
6-cycloheptylcarbonylamino-5-[3-(3,4-methylenedioxyphenethylamino)-2-hydroxy]propoxy-3,4-dihydrocarbostyril,
6-cyclohexylcarbonylamino-5-[3-(4-methoxyphenoxyethylamino)2-hydroxy]propoxy-3,4-dihydrocarbostyril,
6-cyclohexylcarbonylamino-5-[3-(4-phenyl-1-piperazinyl)-2-hydroxy]propoxy-3,4-dihydrocarbostyril,
6-cyclohexylcarbonylamino-3-[3-(3,4-dimethoxyphenethylamino)2-hydroxy]propoxy-3,4-dihydrocarbostyril,
8-methylsulfonylamino-5-(2-hydroxy-3-isopropylamino)propoxy-3,4-dihydrocarbostyril,
8-ethylsulfonylamino-5-(3-amino-2-hydroxy)propoxy-3,4-dihydrocarbostyril,
8-propylsulfonylamino-5-[3-(3,4-dimethoxyphenethylamino)2-hydroxy]propoxy-3,4-dihydrocarbostyril,
8-methylsulfonylamino-5-(2-hydroxy-3-isopropylamino)propoxy-3,4-dihydrocarbostyril,
8-methylsulfonylamino-5-[2-hydroxy-3-(4-o-tolyl-1-piperazinyl)]propoxy-3,4-dihydrocarbostyril,
8-propylsulfonylamino-5-[2-hydroxy-3-(4-m-methoxyphenyl-1-piperazinyl)]propoxy-3,4-dihydrocarbostyril,
8-butylsulfonylamino-5-{3-[1,1-dimethyl-2-(4-methoxyphenoxy)ethylamino]-2-hydroxy}propoxy-3,4-dihydrocarbostyril,
7-methylsulfonylamino-5-(3-tert-butylamino-2-hydroxy)propoxy-3,4-dihydrocarbostyril,
7-isopropylsulfonylamino-5-[3-(3,4-dimethoxyphenethylamino)2-hydroxy]propoxy-3,4-dihydrocarbostyril,
6-ethylsulfonylamino-5-[2-hydroxy-3-(3,5-dimethoxyphenethylamino)]propoxy-3,4-dihydrocarbostyril,
6-methylsulfonylamino-5-(3-isopropylamino-2-hydroxy)propoxy-3,4-dihydrocarbostyril,
6-isopropylsulfonylamino-5-(3-tert-butylamino-2-hydroxy)propoxy-3,4-dihydrocarbostyril,
6-ethylsulfonylamino-5-[3-(3,4-dimethoxyphenethylamino)-2-hydroxy]propoxy-3,4-dihydrocarbostyril,
6-butylsulfonylamino-5-[3-(4-methoxyphenoxyethylamino)-2-hydroxy]propoxy-3,4-dihydrocarbostyril,
6-methylsulfonylamino-5-{3-[1,1-dimethyl-2-(3,4-dimethoxyphenyl)ethylamino]-2-hydroxy}propoxy-3,4-dihydrocarbostyril,
6-methylsulfonylamino-5-[3-(6-phenylhexylamino)-2-hydroxy]propoxy-3,4-dihydrocarbostyril,
6-methylsulfonylamino-5-[2-hydroxy-3-(4-m-methoxyphenyl-1-piperazinyl)]propoxy-3,4-dihydrocarbostyril,
8-p-toluenesulfonylamino-5-(3-isopropylamino-2-hydroxy)propoxy-3,4-dihydrocarbostyril,
8-(3,4-dichlorophenylsulfonylamino)-5-(3-tert-butylamino-2-hydroxy)propoxy-3,4-dihydrocarbostyril,
8-p-toluenesulfonylamino-5-[2-hydroxy-3-(4-methoxyphenoxyethylamino)]propoxy-3,4-dihydrocarbostyril,
8-p-toluenesulfonylamino-[3-(3,5-dimethoxyphenoxyethylamino)2-hydroxy]propoxy-3,4-dihydrocarbostyril,
8-p-toluenesulfonylamino-[3-(4-carbamoylphenoxyethylamino)2-hydroxy]propoxy-3,4-dihydrocarbostyril,
8-p-toluenesulfonylamino-5-[2-hydroxy-3-(3,4-dimethoxyphenethylamino)]propoxy-3,4-dihydrocarbostyril,
8-phenylsulfonylamino-5-[2-hydroxy-3-(3,4-dimethoxyphenethylamino)]propoxy-3,4-dihydrocarbostyril,
8-p-toluenesulfonylamino-5-[2-hydroxy-3-(4-o-methoxyphenyl-1-piperazinyl]propoxy-3,4-dihydrocarbostyril,
8-(3,4-dimethoxyphenylsulfonylamino)-5-[2-hydroxy-3-(3,4-dimethoxyphenethylamino)]propoxy-3,4-dihydrocarbostyril,
7-p-toluenesulfonylamino-5-[3-(3,4-dimethoxyphenethylamino)2-hydroxy]propoxy-3,4-dihydrocarbostyril,
7-p-toluenesulfonylamino-5-[2-hydroxy-3-(4-methoxyphenoxyethylamino)propoxy-3,4-dihydrocarbostyril,
7-p-toluenesulfonylamino-5-[3-(4-p-tolyl-1-piperazinyl)2-hydroxy]propoxy-3,4-dihydrocarbostyril,
6-(3,4-dimethoxyphenylsulfonylamino)-5-[3-(3,4-dimethoxyphenethylamino)-2-hydroxy]propoxy-3,4-dihydrocarbostyril,
6-p-toluenesulfonylamino-5-(3-tert-butylamino-2-hydroxy)propoxy-3,4-dihydrocarbostyril,
6-p-toluenesulfonylamino-5-[3-(4-methoxyphenoxyethylamino)2-hydroxy]propoxy-3,4-dihydrocarbostyril,
6-p-toluenesulfonylamino-5-{3-[1,1-dimethyl-2-(3,4-dimethoxyphenyl)ethylamino]-2-hydroxy}propoxy-3,4-dihydrocarbostyril,
6-p-toluenesulfonylamino-5-[3-(4-phenylbutylamino)-2-hydroxy]propoxy-3,4-dihydrocarbostyril,
6-p-toluenesulfonylamino-5-[3-(4-m-chlorophenyl-1-piperazinyl)-2-hydroxy]propoxy-3,4-dihydrocarbostyril,
8-ureido-5-(3-amino-2-hydroxy)propoxy-3,4-dihydrocarbostyril,
8-ureido-5-(3-tert-butylamino-2-hydroxy)propoxy-3,4-dihydrocarbostyril,
8-ureido-5-[3-(4-carbamoylphenoxyethylamino)-2-hydroxy]propoxy-3,4-dihydrocarbostyril,
8-N-propylcarbamoylamino-5-(2-hydroxy-3-isopropylamino)propoxy-3,4-dihydrocarbostyril,
8-ureido-5-[3-(3,4-dimethoxyphenethylamino)-2-hydroxy]propoxy-3,4-dihydrocarbostyril,
8-ureido-5-[2-hydroxy-3-(4-methoxyphenoxyethylamino)]propoxy-3,4-dihydrocarbostyril,
8-ureido-5-(2-hydroxy-3-phenethylamino)propoxy-3,4-dihydrocarbostyril,
8-ureido-5-[2-hydroxy-3-(3,5-dimethoxyphenethylamino)]propoxy-3,4-dihydrocarbostyril,
8-ureido-5-{3-[1,1-dimethyl-2-(3,4-dimethoxyphenyl)ethylamino]-2-hydroxy}propoxy-3,4-dihydrocarbostyril,
8-ureido-5-[2-hydroxy-3-(4-o-methoxyphenyl-1-piperazinyl)]propoxy-3,4-dihydrocarbostyril,
8-ureido-5-[2-hydroxy-3-(4-phenyl-1-piperazinyl)]propoxy-3,4-dihydrocarbostyril,
8-ureido-5-[2-hydroxy-3-(4-o-chlorophenyl-1-piperazinyl)]propoxy-3,4-dihydrocarbostyril,
8-ureido-5-[2-hydroxy-3-(4-o-tolyl-1-piperazinyl)]propoxy-3,4-dihydrocarbostyril, 8-N-methylcarbamoylamino-5-[2-hydroxy-3-(4-o-ethoxyphenyl-1-piperazinyl)]propoxy-3,4-dihydrocarbostyril, 8-N,N-diethylcarbamoylamino-5-[2-hydroxy-3-(4-o-tolyl-1-piperazinyl)]propoxy-3,4-dihydrocarbostyril, 8-ureido-5-[2-hydroxy-3-(4-o-styryl-1-piperazinyl)]-propoxy-3,4-dihydrocarbostyril, 8-N,N-methylethylcarbamoyl-3-[3-(3,4-dimethoxyphenethylamino)-2-hydroxy]propoxy-3,4-dihydrocarbostyril, 7-ureido-5-(3-tert-butylamino-2-hydroxy)propoxy-3,4-dihydrocarbostyril, 7-ureido-5-[3-(3,4-dimethoxyphenethylamino)-2-hydroxy]propoxy-3,4-dihydrocarbostyril, 6-ureido-5-(3-isopropylamino-2-hydroxy)propoxy-3,4-dihydrocarbostyril, 6-ureido-5-[3-(3,4-dimethoxyphenethylamino)-2-hydroxy]propoxy-3,4-dihydrocarbostyril, 6-ureido-5-[3-(4-methoxyphenenoxyethylamino)-2-hydroxy]propoxy-3,4-dihydrocarbostyril, 6-ureido-5-{3-[1-methyl-2-(3,4-dimethoxyphenyl)ethylamino]-2-hydroxy}propoxy-3,4-dihydrocarbostyril, 6-N-ethylcarbamoylamino-5-(3-phenethylamino-2-hydroxy)propoxy-3,4-dihydrocarbostyril, 6-ureido-5-[3-(3,5-dimethoxyphenethylamino)-2-hydroxy]propoxy-3,4-dihydrocarbostyril, 8-methoxycarbonylamino-5-(3-isopropylamino-2-hydroxy)propoxy-3,4-dihydrocarbostyril, 8-ethoxycarbonylamino-5-[3-(4-carbamoylphenoxyethylamino)-2-hydroxy]propoxy-3,4-dihydrocarbostyril, 8-isopropoxycarbonylamino-5-(3-tert-butylamino-2-hydroxy)propoxy-3,4-dihydrocarbostyril, 8-butoxycarbonylamino-5-[3-(4-methoxyphenoxyethylamino)-2-hydroxy]propoxy-3,4-dihydrocarbostyril, 8-ethoxycarbonylamino-5-[2-hydroxy-3-(3,5-dimethoxyphenethylamino)]propoxy-3,4-dihydrocarbostyril, 8-ethoxycarbonylamino-5-[2-hydroxy-3-(3,4-dimethoxyphenethylamino)]propoxy-3,4-dihydrocarbostyril, 8-ethoxycarbonylamino-5-[2-hydroxy-3-(4-o-methoxyphenyl-1-piperazinyl)]propoxy-3,4-dihydrocarbostyril, 8-butoxycarbonylamino-5-[2-hydroxy-3-(4-m-chlorophenyl-1-piperazinyl)]propoxy-3,4-dihydrocarbostyril, 8-ethoxycarbonylamino-5-{3-[1,1-dimethyl-2-(4-methoxyphenoxy)ethylamino]-2-hydroxy}propoxy-3,4-dihydrocarbostyril, 7-ethoxycarbonylamino-5-(3-isopropylamino-2-hydroxy)propoxy-3,4-dihydrocarbostyril, 7-ethoxycarbonylamino-5-[3-(3,4-dimethoxyphenethylamino)-2-hydroxy]propoxy-3,4-dihydrocarbostyril, 6-ethoxycarbonylamino-5-(3-tert-butylamino-2-hydroxy)propoxy-3,4-dihydrocarbostyril, 6-propoxycarbonylamino-5-[3-(4-methoxyphenoxyethylamino)-2-hydroxy]propoxy-3,4-dihydrocarbostyril, 6-methoxycarbonylamino-5-[3-(3,4-dimethoxyphenethylamino)-2-hydroxy]propoxy-3,4-dihydrocarbostyril, 6-isopropoxycarbonylamino-5-[3-(3,4-ethylenedioxyphenethylamino)-2-hydroxy]propoxy-3,4-dihydrocarbostyril, 6-ethoxycarbonylamino-5-{3-[1,1-dimethyl-2-(3,4-dimethoxy)ethylamino]-2-hydroxy}propoxy-3,4-dihydrocarbostyril, 6-ethoxycarbonylamino-5-[2-hydroxy-3-(4-o-methoxyphenyl-1-piperazinyl)]propoxy-3,4-dihydrocarbostyril, 6-methoxycarbonylamino-5-[2-hydroxy-3-(4-phenyl-1-piperazinyl)]propoxy-3,4-dihydrocarbostyril, 6-ethoxycarbonylamino-5-[2-hydroxy-3-(6-phenylhexylamino)]propoxy-3,4-dihydrocarbostyril, 6-ethoxycarbonylamino-5-[2-hydroxy-3-(3,5-dimethoxyphenethylamino)]propoxy-3,4-dihydrocarbostyril, 8-ureido-5-[2-hydroxy-3-(3,5-dimethoxy-4-chlorophenoxyethylamino)]propoxy-3,4-dihydrocarbostyril, 8-ureido-5-[2-hydroxy-3-(3,4-dimethylphenoxyethylamino)]propoxy-3,4-dihydrocarbostyril, 8-acetylamino-5-[2-hydroxy-3-(4-methylphenethylamino)]propoxy-3,4-dihydrocarbostyril, 8-p-toluenesulfonylamino-5-[2-hydroxy-3-(3,5-dimethylphenoxyethylamino)]propoxy-3,4-dihydrocarbostyril, 8-ethoxycarbonylamino-3-[2-hydroxy-3-(4-chloro-3,5-dimethylphenoxyethylamino)]propoxy-3,4-dihydrocarbostyril, 8-ureido-5-(2-hydroxy-3-morpholino)propoxy-3,4-dihydrocarbostyril, 8-ethoxycarbonylamino-5-(2-hydroxy-3-pyrrolidino)-propoxy-3,4-dihydrocarbostyril, 8-p-toluenesulfonylamino-5-(2-hydroxy-3-pyrrolidino)-propoxy-3,4-dihydrocarbostyril, 8-methylsulfonylamino-5-(2-hydroxy-3-piperidino)-propoxy-3,4-dihydrocarbostyril, 8-acetylamino-5-(2-hydroxy-3-piperidino)propoxy-3,4-dihydrocarbostyril, 8-ethoxycarbonylamino-5-(2-hydroxy-3-piperidino)-propoxy-3,4-dihydrocarbostyril, 8-cyclohexylcarbonylamino-5-(2-hydroxy-3-morpholino)propoxy-3,4-dihydrocarbostyril, 8-acetylamino-5-(2-hydroxy-3-morpholino)propoxy-3,4-dihydrocarbostyril, The present invention is further illustrated by the following Examples, but these examples are given for illustrative purposes only and not to be construed as limiting the present invention. Unless otherwise indicated, all parts, percents, ratios and the like are by weight.

REFERENCE EXAMPLE 1

2 g of 5-hydroxy-8-amino-3,4-dihydrocarbostyril was suspended in 20 ml of methanol, and 10 ml of acetic anhydride was added to the suspension. The mixture was stirred at room temperature for 2 hours and the precipitated crystals were recovered by filtration. The crystals were recrystallized from water to obtain 2 g of colorless needle crystals having a melting point of 284°–286° C. (with decomposition). The product thus obtained was found to be 5-hydroxy-8-acetamido-3,4-dihydrocarbostyril by NMR and IR spectra and elementary analysis.

REFERENCE EXAMPLE 2

8.0 g of 8-acetylamino-5-hydroxy-3,4-dihydrocarbostyril was suspended in 100 ml of epichlorohydrin, and the suspension was stirred at a temperature of 60° C. for 2 hours in the presence of 1.0 ml of piperidine as a catalyst. After completion of the reaction, the reaction mixture was concentrated to dryness under reduced pressure, and diethyl ether was added to the residue under ice-cooling to crystallize the product. The crystals thus formed were recovered by filtration, washed with 200 ml of diethyl ether, dried and recrystallized from ethanol to obtain 6.01 g of 8-acetylamino-5-(3-chloro-2-hydroxy)propoxy-3,4-dihydrocarbostyril as colorless crystals having a melting point of 158.0°–160.4° C.

REFERENCE EXAMPLE 3

4.5 g of 6-acetylamino-5-hydroxy-3,4-dihydrocarbostyril was suspended in 50 ml of epichlorohydrin, and the suspension was stirred at a temperature of 70° C. for 3 hours in the presence of a drop of piperidine as a catalyst. After completion of the reaction, any excess of unreacted epichlorohydrin was removed under reduced pressure, and water was added to the residual tarlike substance followed by concentration to dryness under reduced pressure. A small volume of methanol was then added to the resulting residue while cooling with ice to crystallize the product. The crystals thus obtained were recovered by filtration, washed with diethyl ether, dried and recrystallized from methanol to obtain 3.56 g of 6-acetylamino-5-(3-chloro-2-hydroxy)propoxy-3,4-dihydrocarbostyril as light yellow crystals having a melting point of 177.0°–178.4° C.

REFERENCE EXAMPLE 4

6.0 g of 8-cyclohexylcarbonylamino-5-hydroxy-3,4-dihydrocarbostyril was suspended in 50 ml of epichlorohydrin, and the suspension was stirred at a temperature of 70° C. for 5 hours in the presence of 1 ml of triethylamine. After completion of the reaction, the reaction mixture was concentrated to dryness under reduced pressure, and the residue was dissolved in 300 ml of chloroform. The resulting chloroform solution was washed with water, and the chloroform was removed by distillation under reduced pressure. The residue was dissolved in 50 ml of hot ethanol and any insoluble materials were removed by filtration. The filtrate was then allowed to cool to crystallize the product. The crystals thus obtained were recovered by filtration, washed with cold ethanol and dried to obtain 2.53 g of 8-cyclohexylcarbonylamino-5-(3-chloro-2-hydroxy)-propoxy-3,4-dihydrocarbostyril as colorless powdery crystals having a melting point of 204.0° to 205.6° C.

REFERENCE EXAMPLES 5 to 8

The following compounds were prepared in accordance with the procedure as described in Reference Example 2.

| Reference Example Nos. | X | $R_1$ | Solvent for Recrystallization | Melting Points (° C.) |
|---|---|---|---|---|
| 5 | Cl | —$CONH_2$ | Chloroform-Methanol | Gradual Decomposition over 180° C. |
| 6 | Cl | —$COOC_2H_5$ | Ethanol | 183.2–185.8 |
| 7 | Cl | —$SO_2CH_3$ | Methanol | 233.8–237.0 |
| 8 | Cl | —$SO_2$—C$_6$H$_4$—$CH_3$ | Methanol | 187.8–189.4 |

REFERENCE EXAMPLE 9

10.7 g of 8-amino-5-hydroxy-3,4-dihydrocarbostyril hydrochloride was dissolved in 300 ml of water, and a solution of 4.06 g of potassium cyanide dissolved in 100 ml of water was added thereto while stirring at a temperature of 50° C. After stirring the mixture for one hour at 50° C., the precipitated crystals were recovered by filtration, washed successively with 1 l of water and methanol to obtain 8.75 g of 5-hydroxy-8-ureido-3,4-dihydrocarbostyril as colorless amorphous crystals having a melting point of 209.0°–211.2° C.

REFERENCE EXAMPLE 10

10.7 g of 8-amino-5-hydroxy-3,4-dihydrocarbostyril hydrochloride was dissolved in 200 ml of a 10% aqueous sodium hydroxide solution, 5.4 g of ethyl chlorocarbonate was added to the solution while stirring at room temperature followed by stirring for one hour at 30° C. After completion of the reaction, the reaction mixture was rendered acidic with hydrochloric acid under ice-cooling, the precipitated crystals were recovered by filtration, washed with water and dried. Recrystallization of the dried crystals from ethanol yielded 7.95 g of 8-ethoxycarbonylamino-5-hydroxy-3,4-dihydrocarbostyril as colorless needle crystals having a melting point of 283.8°–284.6° C.

REFERENCE EXAMPLE 11

5.0 g of 8-amino-5-hydroxy-3,4-dihydrocarbostyril was suspended in 30 ml of acetic acid, and 4.0 g of sodium acetate was added to the suspension while stirring. 3.5 g of methanesulfonyl chloride was then added to the mixture followed by heating for 7 hours while refluxing. After completion of the reaction, 100 ml of water was added to the reaction mixture which was then concentrated to dryness under reduced pressure. The resulting residue was added to 200 ml of water, and the mixture was stirred. The crystals formed were recovered by filtration, washed with water and recrystallized from methanol to obtain 3.89 g of 5-hydroxy-8-methanesulfonylamino-3,4-dihydrocarbostyril as colorless amorphous crystals having a melting point of 269.4°–269.8° C.

REFERENCE EXAMPLE 12

8.00 g of 5-hydroxy-8-ureido-3,4-dihydrocarbostyril was suspended in 50 ml of methanol, and 50 ml of epichlorohydrin and 2 ml of piperazine were added to the suspension followed by heating for 2 hours while refluxing. After completion of the reaction, the reaction mixture was allowed to cool and the precipitated crystals were recovered by filtration. The crystals were washed with methanol and recrystallized from a mixture of chloroform and methanol to obtain 8.36 g of 5-(3-chloro-2-hydroxy)propoxy-8-ureido-3,4-dihydrocarbostyril as colorless amorphous crystals having a melting point of 225°–230° C. (with decomposition).

REFERENCE EXAMPLE 13

10.7 g of 8-amino-5-hydroxy-3,4-dihydrocarbostyril was dissolved in 100 ml of pyridine, and 10.0 g of cyclohexylcarbonyl chloride was added to the solution while vigorously stirring at room temperature followed by stirring at 50° C. for 30 minutes. The precipitated crystals were recovered by filtration, washed with ethanol, dried and dissolved in 200 ml of a 10% aqueous sodium hydroxide solution. Activated carbon was added to the solution, and the mixture was stirred and filtered. The filtrate was rendered acidic with hydrochloric acid under ice cooling, and the precipitated crystals were recovered by filtration, washed with water and dried. Recrystallization from methanol yielded 6.6 g of 8-cyclohexylcarbonylamino-5-hydroxy-3,4-dihydrocarbostyril as colorless amorphous crystals having a melting point of 304.2°–304.8° C.

EXAMPLE 1

3.0 g of 8-acetylamino-5-(3-chloro-2-hydroxy)propoxy-3,4-dihydrocarbostyril was suspended in 20 ml of methanol, and 3.0 g of 3,4-dimethoxyphenethylamine and 1.0 ml of triethylamine were added to the solution followed by heating for 8 hours while refluxing. After completion of the reaction, the reaction mixture was concentrated to dryness under reduced pressure, and 30 ml of diethyl ether was added to the residual tar-like substance. The mixture was thoroughly stirred and the ethereal layer was removed by decantation, the above procedure, i.e., addition of diethyl ether and stirring followed by decantation, was repeated three times, and residue finally obtained was dissolved in 30 ml of isopropanol. Hydrogen chloride gas was then blown into the solution, and the precipitated crystals were recovered by filtration and recrystallized from diethyl ether to obtain 2.67 g of 8-acetylamino-5-[3-(3,4-dimethoxyphenethylamino)-2-hydroxy]propoxy-3,4-dihydrocarbostyril hydrochloride as colorless powdery crystals having a melting point of 203.8°–206.4° C.

EXAMPLE 2

1.0 g of 5-(3-chloro-2-hydroxy)propoxy-8-ureido-3,4-dihydrocarbostyril was suspended in 100 ml of methanol, and 1.3 g of 4-methoxyphenoxyethylamine was added to the solution followed by heating for 8 hours while refluxing. After completion of the reaction, the reaction mixture was allowed to cool, and the precipitated crystals were recovered by filtration. The crystals were washed with 200 ml of cold methanol and dried. The crystals thus obtained were then dissolved in 100 ml of a saturated methanolic hydrochloric acid, and, after decoloration treatment with activated carbon, the solution was cooled with ice to crystallize the product. The crystals were recovered by filtration, washed with cold methanol and dried to obtain 0.94 g of of 5-[2-hydroxy-3-(4-methoxyphenoxyethylamino)]propoxy-8-ureido-3,4-dihydrocarbostyril hydrochloride as colorless powdery crystals having a melting point of 191.8°–193.6° C.

EXAMPLE 3

0.8 g of 5-(3-chloro-2-hydroxy)propoxy-8-ethoxycarbonylamino-3,4-dihydrocarbostyril was suspended in 10 ml of ethanol, and 1.4 g of 3,4-dimethoxyphenethylamine was added to the solution followed by heating for 6 hours while refluxing. After completion of the reaction, the reaction mixture was concentrated under reduced pressure, the resulting residue was added to 300 ml of diethyl ether while stirring. The precipitated tar-like substance was separated and dissolved in ethanol. The solution was then adjusted to a pH of about 3 to 4 with concentrated hydrochloric acid and decolored. Diethyl ether was added to the solution until the solution became white turbid, and the mixture was allowed to cool to obtain 0.38 g of 5-[3-(3,4-dimethoxyphenethylamino)-2-hydroxy]propoxy-8-ethoxycarbonylamino-3,4-dihydrocarbostyril hydrochloride as colorless powdery crystals having a melting point of 154.0°–157.0° C. (with decomposition).

EXAMPLE 4

0.5 g of 5-(3-chloro-2-hydroxy)propoxy-8-cyclohexylcarbonylamino-3,4-dihydrocarbostyril was suspended in 20 ml of methanol, and 0.73 g of 4-methoxyphenoxyethylamine was added to the suspension followed by heating for 10 hours while refluxing. After completion of the reaction, the reaction mixture was concentrated under reduced pressure and the resulting residue was added to 200 ml of diethyl ether while stirring vigorously. An ether-insoluble material was separated and dissolved in 50 ml of ethanol. The ethanolic solution was adjusted to a pH of about 3-4 with hydrochloric acid, treated with activated carbon to decolor the solution and again concentrated to dryness under reduced pressure. The residue thus obtained was recrystallized from ethanol to obtain 0.37 g of 8-cyclohexylcarbonylamino-5-[2-hydroxy-3-(4-methoxyphenoxyethylamino)]propoxy-3,4-dihydrocarbostyril hydrochloride as colorless powdery crystals having a melting point of 188.0°–190.0° C.

EXAMPLE 5

1.0 g of 6-acetylamino-5-(3-chloro-2-hydroxy)propoxy-3,4-dihydrocarbostyril was suspended in 50 ml of methanol, and 50 ml of isopropylamine was added to the suspension followed by heating for 8 hours while refluxing. After completion of the reaction, the reaction mixture was concentrated to dryness, and the remaining tar-like substance was dissolved in dilute hydrochloric acid. Any insoluble materials were separated by filtration, and the filtrate was adjusted to a pH of about 10 with a 10% aqueous sodium carbonate solution. The resulting alkaline aqueous solution was then extracted with 5 times with 100 ml portions of chloroform, and the combined chloroform extracts were dried over anhydrous sodium carbonate, followed by filtration to remove sodium carbonate. The chloroform was removed by distillation, and the residual tar-like substance was dissolved in 50 ml of acetone. The solution was treated with activated carbon to decolor the solution, adjusted to a pH of about 4–5 with a solution of oxalic acid in acetone, and allowed to cool. The precipitated crystals were recovered by filtration, washed thoroughly with cold acetone and dried obtain 0.73 g of 6-acetylamino-5-(2-hydroxy-3-isopropylamino)-propoxy-3,4-dihydrocarbostyril oxalate as colorless powdery crystals having a melting point of 199.0°–201.0° C.

EXAMPLE 6

0.67 g of 5-(3-chloro-2-hydroxy)propoxy-8-p-toluenesulfonylamino-3,4-dihydrocarbostyril was suspended in 20 ml of methanol, and 1.2 g of 3,4-dimethoxyphenethylamine was added to the suspension followed by heating for 10 hours while refluxing. After completion of the reaction, the reaction mixture was concentrated under reduced pressure, and the residue was added to 200 ml of diethyl ether followed by thoroughly stirring. The precipitated ether-insoluble material was separated, and dissolved in 50 ml of ethanol. The resulting solution was adjusted to a pH of about 4 with concentrated hydrochloric acid and concentrated to dryness under reduced pressure. The residue was dissolved in 10 ml of methanol and treated with activated carbon to decolor the solution. 50 ml of isopropanol was added to the solution and the mixture was allowed to cool to crystallize the product. The crystals thus obtained were recovered by filtration, washed thoroughly with cold isopropanol and dried to obtain 0.37 g of 5-[3-(3,4-dimethoxyphenethylamino)-2-hydroxy]-8-p-toluenesulfonylamino-3,4-dihydrocarbostyril hydrochloride as colorless powdery crystals having a melting point of 147.0°–149.0° C.

EXAMPLE 7

3.0 g of 5-hydroxy-8-methanesulfonylamino-3,4-dihydrocarbostyril was suspended in 10 ml of epichlorohydrin, and 2 ml of triethylamine was added to the suspension followed by heated at a temperature of 70° C. for 5 hours while refluxing. After completion of the reaction, the reaction mixture was concentrated under reduced pressure, and the residual tar-like substance was dissolved in 100 ml of chloroform. The chloroform solution was washed 3 times with 100 ml portions of water and concentrated under reduced pressure. 100 ml of water was added to the residue and the mixture was again concentrated. The residual tar-like substance was dissolved in methanol, and 50 ml of isopropylamine was added to the solution followed by heating for 8 hours while refluxing. After completion of the reaction, the reaction mixture was concentrated to dryness under reduced pressure, and the residue was dissolved in 10 ml of dilute hydrochloric acid. Any insoluble materials were removed by filtration and the filtrate was adjusted to a pH of about 10 with a 10% aqueous sodium carbonate solution followed by extraction with 200 ml of chloroform. The chloroform solution was dried over anhydrous sodium carbonate which was then removed by filtration. The filtrate was concentrated to dryness under reduced pressure, and the residue was dissolved in 10 ml of ethanol. The solution was adjusted to a pH of about 4 with concentrated hydrochloric acid, and concentrated to dryness under reduced pressure. The resulting residue was recrystallized from isopropanol to obtain 0.27 g of 5-[2-hydroxy-3-(isopropylamino)]-propoxy-8-methanesulfonylamino-3,4-dihydrocarbostyril as colorless powdery crystals having a melting point of 149.0°–151.0° C.

EXAMPLES 8 to 21

According to the procedure as described in the previous Examples, the following compounds were prepared.

Structure:

$$R_1HN-\text{[benzene ring with}-OCH_2CHCH_2NR_2R_3\text{ (OH on middle CH)}]-\underset{H}{N}-\overset{O}{C}- \cdot HX$$

| Example Nos. | Position of R₁HN-Group | R₁ | R₂ | R₃ | HX | Procedure | Solvent for Recrystallization | Melting Point (°C.) |
|---|---|---|---|---|---|---|---|---|
| 8 | 8 | C₂H₅OCO— | H | —CH₂CH₂—O—⟨⟩—CONH₂ | — | Example 1 | Methanol | 212.5–214.0 |
| 9 | 8 | H₂N—C(=O)— | H | —CH(CH₃)—CH₂—⟨Ph⟩ | HCl | Example 3 | Water-Methanol | 178.0–178.8 |
| 10 | 8 | H₂N—C(=O)— | H | —CH(CH₃)—⟨benzene with OCH₃⟩ | HCl | Example 3 | Ethanol | 213.6–214.8 |
| 11 | 8 | H₂N—C(=O)— | H | —CH₂CH₂—O—⟨benzene with CH₃, OCH₃⟩ | HCl | Example 3 | Ethanol | 179.0–181.0 |
| 12 | 8 | O=C—⟨cyclohexyl⟩ | H | —CH(CH₃)—CH₂—⟨Ph⟩ | HCl | Example 5 | Ethanol | 216.4–217.2 |
| 13 | 8 | O=C—⟨cyclohexyl⟩ | H | —CH(CH₃)—⟨benzene with OCH₃⟩ | HCl | Example 5 | Ethanol | 153.2–155.8 |
| 14 | 8 | H₂N—C(=O)— | H | —CH₂CH₂—O—⟨benzene with CH₃, OCH₃⟩ | HCl | Example 3 | Ethanol-Water | 199.0–201.0 (with decomp.) |
| 15 | 8 | C₂H₅O—C(=O)— | H | —C(CH₃)₃ | HCl | Example 4 | Ethanol-Ethyl Acetate | 194.6–196.0 |
| 16 | 8 | CH₃—⟨C₆H₄⟩—SO₂— | H | —C(CH₃)₃ | HCl | Example 7 | Methanol-Isopropanol | 187.0–189.0 |
| 17 | 8 | CF₃CO— | H | —CH₂CH₂—O—⟨⟩—OCH₃ —CH(CH₃)₂ | COOH COOH | Example 6 | Ethanol-Acetone | 193.0–195.0 |

-continued structure: R1HN-substituted phenyl ring with OCH₂CHCH₂NR₂R₃ (with OH on middle carbon) ·HX, and a —N(H)—C(=O)— group ortho substituent

| Example Nos. | Position of R₁HN-Group | R₁ | R₂ | R₃ | HX | Procedure | Solvent for Recrystallization | Melting Point (°C) |
|---|---|---|---|---|---|---|---|---|
| 18 | 6 | CH₃CO— | H | —CH₂CH₂—O—⌬—OCH₃ (with OCH₃) | — | Example 1 | Methanol | 178.0–181.0 |
| 19 | 6 | CH₃CO— | H | —CH₂CH₂—O—⌬—OCH₃ (with OCH₃) | — | Example 1 | Isopropanol | 161.2–163.4 |
| 20 | 8 | CH₃CO— | —CH₂—C₆H₅ | —CH₂CH₂—O—⌬—CONH₂ | HCl | Example 7 | Methanol-Isopropanol | 173.0–176.0 |
| 21 | 8 | CH₃—⌬—SO₂— | H | —CH₂CH₂—O—⌬—CONH₂ | HCl | Example 7 | Methanol-Isopropanol | 181.5–185.0 |

EXAMPLE 22

2.0 g of 5-(3-chloro-2-hydroxy)propoxy-8-ureido-3,4-dihydrocarbostyril was suspended in 100 ml of methanol, 2.0 g of 1-p-methoxyphenylpiperazine was added to the suspension followed by heating for 4 hours while refluxing. After completion of the reaction, the reaction mixture was cooled with ice, and the precipitated crystals were recovered by filtration. The crystals thus obtained were washed with water and then cold methanol, and dried. The dried crystals were dissolved in dilute hydrochloric acid and any insoluble materials were removed by filtration. Ethanol was then added to the filtrate in an amount twice the volume of the filtrate, and the mixture was refluxed for 1 hour. Any insoluble materials were removed by filtration, and the filtrate was treated with activated carbon for decoloration to obtain 0.72 g of 5-[2-hydroxy-3-(4-p-methoxyphenyl-1-piperazinyl)]propoxy-8-ureido-3,4-dihydrocarbostyril hydrochloride as colorless amorphous crystals having a melting point of 217°-220° C. (with decomposition).

EXAMPLE 23

2.0 g of 8-acetylamino-5-(3-chloro-2-hydroxy)-propoxy-3,4-dihydrocarbostyril was suspended in 100 ml of methanol, and 2.0 ml of 4-o-methoxyphenylpiperazine was added to the suspension followed by heating for 5 hours while refluxing. After completion of the reaction, the reaction mixture was allowed to cool, and the precipitated crystals were recovered by filtration. The crystals were washed with cold ethanol and added to 100 ml of a saturated ethanolic hydrochloric acid followed by heating for one hour while refluxing. After removal of any insoluble materials by filtration, the filtrate was subjected to decoloration treatment with activated carbon, and concentrated to dryness under reduced pressure. The residue thus obtained was then recrystallized from 50 ml of a mixture of ethanol and methanol (1:1 by volume) to obtain 0.92 g of 8-acetylamino-5-[2-hydroxy-3-(4-o-methoxyphenyl-1-piperazinyl)]propoxy-3,4-dihydrocarbostyril hydrochloride as colorless amorphous crystals having a melting point of 215°-218.0° C. (with decomposition).

EXAMPLE 24

3.0 g of 5-(3-chloro-2-hydroxy)propoxy-8-ureido-3,4-dihydrocarbostyril and 3.0 g of 1-o-tolylpiperazine were dissolved in 100 ml of a mixture of acetonitrile and methanol (2:1 by volume), and the mixture was then heated for 5 hours while refluxing. After completion of the reaction, the reaction mixture was concentrated to dryness under reduced pressure and the resulting residue was dissolved in 50 ml of dilute hydrochloric acid followed by allowing the solution to cool. The precipitated crystals were removed by filtration, and the filtrate was concentrated to a volume of 10 ml under reduced pressure. Ethanol was then added to the concentrate until the mixture became white turbid, and the mixture was heated to obtain a clear solution which was then subjected to decoloration treatment with activated carbon and allowed to cool. The precipitated crystals were separated by filtration, washed with ethanol and dried to obtain 1.33 g of 5-[2-hydroxy-3-(4-o-tolyl-1-piperazinyl)]propoxy-8-ureido-3,4-dihydrocarbostyril hydrochloride as colorless amorphous crystals having a melting point of 228°-232.0° C.

EXAMPLE 25

3.0 g of 5-(3-chloro-2-hydroxy)propoxy-8-ureido-3,4-dihydrocarbostyril and 4.0 g of 1-o-methoxyphenylpiperazine were heated for 8 hours while refluxing in a mixture of acetonitrile and methanol (2:1 by volume). After completion of the reaction, the reaction mixture was concentrated to dryness under reduced pressure, and the residue was added to 200 ml of diethyl ether. After stirring vigorously, the mixture was allowed to stand, and the precipitated crystals were recovered by filtration and washed with diethyl ether. The crystals thus obtained were dissolved in methanol and the mixture was boiled. Any insoluble materials were separated by filtration and the filtrate was cooled with ice. Hydrogen chloride gas was then blown into the filtrate while ice-cooling. The precipitated crystals were separated by filtration, washed with cold methanol and dried to obtain 2.80 g of 5-[2-hydroxy-3-(4-o-methoxyphenyl-1-piperazinyl)]propoxy-8-ureido-3,4-dihydrocarbostyril hydrochloride as colorless pyramidic crystals having a melting point of 211°-213.0° C. (with decomposition).

EXAMPLE 26

3.0 g of 5-(3-chloro-2-hydroxy)propoxy-8-ureido-3,4-dihydrocarbostyril was suspended in 100 ml of methanol, and 3.0 g of 1-m-chlorophenylpiperazine hydrochloride and 3.0 g of sodium carbonate were added to the suspension followed by heated for 8 hours while refluxing. After completion of the reaction, the reaction mixture was allowed to cool and the precipitated crystals were filtered. The crystals were washed with water to remove any remaining inorganic materials, and the crystals were washed with ethanol followed by drying. The dried crystals were added to 150 ml of 50% aqueous ethanol and the mixture was rendered acidic with hydrochloric acid followed by heating while refluxing to obtain a clear solution. The solution was filtered to remove any insoluble materials, and the filtrate was subjected to decoloration treatment followed by allowing the filtrate to cool. The precipitated crystals were recovered by filtration, washed with ice-cooled water and dried to obtain 0.86 g of 5-[2-hydroxy-3-(4-m-chlorophenyl-1-piperazinyl)]propoxy-8-ureido-3,4-dihydrocarbostyril hydrochloride as colorless amorphous crystals having a melting point of 220°-222.5° C. (with decomposition).

EXAMPLE 27

1.5 g of 5-(3-chloro-2-hydroxy)propoxy-8-ureido-3,4-dihydrocarbostyril was suspended in 20 ml of methanol, and 5 ml of 1-phenylpiperazine was added to the suspension followed by heating for 8 hours while refluxing. After completion of the reaction, the reaction mixture was concentrated to dryness under reduced pressure, and the residue was dissolved in 50 ml of methanol. The solution was ice-cooled to crystallize the product. The crystals thus obtained were separated by filtration, washed with cold methanol and dissolved in 50 ml of 1N hydrochloric acid. The mixture was then filtered to remove any insoluble materials, and the filtrate was subjected to decoloration treatment. Ethanol was then added to the filtrate until the filtrate became white turbid, and the mixture was heated to obtain a clear solution. The solution was allowed to cool to obtain 0.54 g of 5-[2-hydroxy-3-(4-phenyl-1-piperazinyl)]propoxy-8-ureido-3,4-dihydrocarbostyril hydrochloride as colorless amorphous crystals having a melting point of 196°–198.0° C. (with decomposition).

EXAMPLE 28

5.0 g of 8-ethoxycarbonylamino-5-hydroxy-3,4-dihydrocarbostyril was suspended in 50 ml of methanol, and 50 ml of epichlorohydrin was added to the suspension followed by heating for 8 hours while refluxing in the presence of 3 drops of piperidine as a catalyst. After completion of the reaction, the reaction mixture was concentrated to dryness under reduced pressure. A small amount of ethanol and 4 g of 1-o-methoxypiperazine were added to the residue and the mixture was heated while refluxing for 8 hours. After completion of the reaction, an excess of diethyl ether was added to the reaction mixture while vigorous stirring followed by allowing the mixture to cool. The supernatant was removed and the precipitate was washed with diethyl ether and dried. The dried solid was dissolved in 50 ml of dilute hydrochloric acid while heating, and any insoluble materials were removed by filtration. The filtrate was then concentrated to dryness under reduced pressure, and the resulting residue was recrystallized from ethanol to obtain 1.6 g of 8-ethoxycarbonylamino-5-[2-hydroxy-3-(4-o-methoxyphenyl-1-piperazinyl)]-propoxy-3,4-dihydrocarbostyril hydrochloride as colorless amorphous crystals having a melting point of 218.0°–221.0° C. (with decomposition).

EXAMPLE 29

5.0 g of 5-hydroxy-8-methanesulfonylamino-3,4-dihydrocarbostyril was suspended in 50 ml of methanol, and 50 ml of epichlorohydrin and 1 ml of piperidine were added to the suspension followed by heating for 8 hours while refluxing. After completion of the reaction, the reaction mixture was concentrated to dryness under reduced pressure and the residue was dissolved in 100 ml of methanol. 5.0 g of 1-o-tolylpiperazine hydrochloride and 5.0 g of potassium carbonate were added to the solution, and the mixture was heated for 8 hours while refluxing followed by concentration to dryness under reduced pressure. After washing the residue with water, it was dissolved in dilute hydrochloric acid and any insoluble materials were removed by filtration. The filtrate was subjected to decoloration treatment with activated carbon and concentrated to dryness under reduced pressure. The residue was recrystallized from ethanol to obtain 0.93 g of 5-[2-hydroxy-3-(4-o-tolyl-1-piperazinyl)]propoxy-8-methanesulfonylamino-3,4-dihydrocarbostyril hydrochloride as colorless amorphous crystals having a melting point of 206°–209.0° C. (with decomposition).

EXAMPLE 30

3.0 g of 8-cyclohexylcarbonylamino-5-(3-chloro-2-hydroxy)propoxy-3,4-dihydrocarbostyril was dissolved in 50 ml of methanol, and 8 g of 1-phenylpiperazine was added to the solution followed by heating for 5 hours while refluxing. After completion of the reaction, the reaction mixture was concentrated to dryness, and the residue was washed with diethyl ether followed by drying. The dried solid was dissolved in dilute hydrochloric acid and, after removal of any insoluble materials by filtration, the filtrate was subjected to decoloration treatment and again concentrated to dryness the residue was then recrystallized from ethanol to obtain 1.8 g of 8-cyclohexylcarbonylamino-5-[2-hydroxy-3-(4-phenyl-1-piperazinyl)]propoxy-3,4-dihydrocarbostyril hydrochloride as colorless amorphous crystals having a melting point of 187°–190° C. (with decomposition).

REFERENCE EXAMPLE 14

The $\beta$-adrenergic blocking activity of the compounds of this invention was determined as follows:

Male hybrid adult dogs, weighing 10 to 16 kg, were anesthesized with sodium pentobarbital administered intravenously at a level of 30 mg/kg of body weight, and a cannula was inserted into the trachea of each of the anesthesized dogs. In order to avoid blood coagulation, heparin was administered intravenously at a level of 1000 units and thereafter a cannula was inserted into the right femoral artery. The experiments were conducted under artificial respiration at a rate of 20 ml/kg, 18 r.p.m.

The blood pressure was determined using a pressure tranducer (MPU-0.5 Type, tradename of Nippon Koden Co., Japan) and the heart rate (HR) was determined from the pulse wave of blood pressure using an instantaneous heart rate tachometer (2130 Type, tradename of Sanei Sokki Co., Japan). The air-way resistance (AR) was determined according to the Konzett-Rossler Method (Konzett H. & Rossler R., "Versuchsanordnug zu Untersuchungen an der Bronchial Moskolatur" Arch. Exp. Path., Pharmak, 195 71–74, 27–40 (1940) using a low-pressure type pressure tranducer (LPU-0.1, tradename of Nippon Koden Co., Japan).

The above parameters were continuously recorded on a polygraph (8S 28 Type, tradename of Sanei Sokki Co., Japan). During the experiment, gallamine was administered intravenously at a dosage of 3 mg/kg at one-hour intervals to avoid fluctuation of air-way resistance.

The $\beta$-adrenergic blocking activity of each of the test compounds was evaluated in terms of antagonism (Inhibition %) to the depression at the diastolic blood pressure (dBP) and to the increase in the heart rate induced by the intravenous administration of isoprenaline (1 $\mu$g/kg) and in terms of antagonism (Inhibition %) to the depression by isoprenaline in increase of air-way resistance which was induced by intravenous administration of histamine (5 $\mu$g/kg). In this case, histamine was administered 45 seconds after the administration of isoprenaline.

The $\beta$-adrenergic blocking activity of the test compounds was determined 10 minutes after the intravenous administration of the test compounds at a level of 300 $\mu$g/kg and the results obtained are shown in Table below, where Practolol, Atenolol, 5-(3-t-butylamino-2-hydroxy)propoxy-3,4-dihydrocarbostyril hydrochloride, 8-acetylamino-5-(3-t-butylamino-2-hydroxy)-propoxy-3,4-dihydrocarbostyril hydrochloride and 5-(3,4-dimethoxyphenethylamino-2-hydroxy)propoxy-3,4-dihydrocarbostyril hydrochloride were used as control compounds.

Table 1

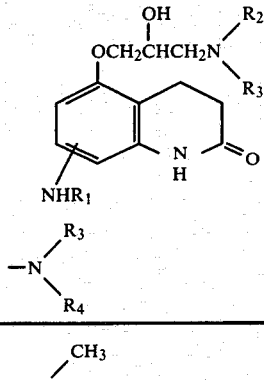

| Sample No. | Type and Position of —NHR₁ Group | −N(R₃)(R₄) | HA | Inhibition (%) HR*¹ | dBP*² | AR*³ |
|---|---|---|---|---|---|---|
| 1 | 6-NHCOCH₃ | −NHCH(CH₃)₂ | HCl | 25.3 | 17.8 | 11.3 |
| 2 | 8-NHCOCH₃ | −NHCH₂CH₂−(3,4-(OCH₃)₂-C₆H₃) | HCl | 30.2 | 25.5 | 10.8 |
| 3 | 8-NHCONH₂ | −NHCH₂CH₂O−(4-OCH₃-C₆H₄) | HCl | 39.6 | 31.8 | 14.7 |
| 4 | 8-NHCOC₂H₅ | −NHCH₂CH₂O−(4-CONH₂-C₆H₄) | HCl | 47.3 | 3.4 | 2.5 |
| 5 | 8-NHCO-cyclohexyl | −NHCH(CH₃)−C₆H₅ | HCl | 53.3 | 42.4 | 23.2 |
| 6 | 6-NHCOCH₃ | −NHCH₂CH₂−(3,4-(OCH₃)₂-C₆H₃) | Free | 37.2 | 11.3 | 12.6 |
| 7 | 8-NHSO₂−(4-CH₃-C₆H₄) | −NHCH₂CH₂O−(4-CONH₂-C₆H₄) | HCl | 26.8 | 11.4 | 10.2 |
| 8 | 8-NHSO₂CH₃ | 4-(2-CH₃-C₆H₄)-piperazin-1-yl | HCl | 21.0 | 6.4 | 7.1 |
| 9 | 8-NHCONH₂ | 4-(2-Cl-C₆H₄)-piperazin-1-yl | HCl | 23.6 | 15.3 | 8.9 |
| 10 | 8-NHCOCH₃ | 4-(2-OCH₃-C₆H₄)-piperazin-1-yl | HCl | 21.7 | 11.6 | 6.2 |

| Sample No. | Control Compounds | | | Inhibition (%) HR*¹ | dBP*² | AR*³ |
|---|---|---|---|---|---|---|

Table 1-continued

| # | Structure | | | |
|---|---|---|---|---|
| 11 | (quinolinone with OCH₂CHCH₂NR₂R₃ at 5-position, OH, NHR₁ at 7) | 100 | 100 | 100 |
| 12 | (3,4-dihydroquinolin-2(1H)-one, 5-OCH₂CH(OH)CH₂NHC(CH₃)₃ · HCl) | 36.8 | 44.2 | 47.6 |
| 13 | (3,4-dihydroquinolin-2(1H)-one, 5-OCH₂CH(OH)CH₂NHCH(CH₃)₂, 8-NHCOCH₃ · HCl) | 87.2 | 65.6 | 79.1 |
| 14 | (Practolol): CH₃CONH—C₆H₄—OCH₂CH(OH)CH₂NHCH(CH₃)₂ | 44.6 | 1.7 | 36.2 |
| 15 | (Atenolol): H₂NCOCH₂—C₆H₄—OCH₂CH(OH)CH₂NHCH(CH₃)₂ | 32.8 | 17.2 | 4.9 |

*¹HR = Heart Rate  
*²dBP = Diastolic Blood Pressure  
*³AR = Air-Way Resistance Further, the acute toxicity of the compounds of the present invention having the formula (I) was determined by intravenous administration (i.v.) and oral administration (p.o.) in 5 to 6 groups of rats (dd strain; body weight, 18 to 22 g; 10 rats in each group) which have been fasted for 12 hours prior to the test. Typical compounds of the present invention of the formula (I), i.e., the compounds of Sample Nos. 2, 3, 4, 6, 7 and 10 showin in Table 1 above, were found to have the LD₅₀ values (50% lethal dose) as shown in Table 2 below.

Table 2

| Compounds (Sample Nos.) | Sex of Rats tested | i.v. | p.o. |
|---|---|---|---|
| 2 | Male | 158 mg/kg | 1350 mg/kg |
| 2 | Female | 142 mg/kg | 1230 mg/kg |
| 3 | Male | 156 mg/kg | 1340 mg/kg |
| 4 | Male | 145 mg/kg | 1210 mg/kg |
| 6 | Male | 160 mg/kg | 1380 mg/kg |
| 7 | Male | 115 mg/kg | 1120 mg/kg |
| 10 | Male | 125 mg/kg | 1170 mg/kg |

The compounds of the present invention can be administered at a dosage level of from about 40 μg to about 2 mg/kg/day by oral, intravenous, intramuscular or intrarectal administration. Typical examples of suitable formulations are given below, but it is to be noted that other dosage forms can also be prepared using other compounds of this invention as well as other excipients which are well known to one skilled in the art, according to the well-established pharmaceutical techniques.

FORMULATION 1

Tablets each containing the following components were prepared from the following components:

| Components | Amount |
| --- | --- |
| 8-Acetylamino-5-[3-(3,4-dimethoxyphenethyl-amino)-2-hydroxy]propoxy-3,4-dihydrocarbostyril | 5 mg |
| Corn Starch | 142 mg |
| Magnesium Stearate | 18 mg |
| Lactose | 45 mg |
| Total | 200 mg |

FORMULATION 2

Tablets each containing the following components were prepared from the following components:

| Components | |
| --- | --- |
| 8-Acetylamino-5-[3-(3,4-dimethoxyphenethyl-amino)-2-hydroxy]propoxy-3,4-dihydrocarbostyril | 10 mg |
| Corn Starch | 140 mg |
| Magnesium Stearate | 18 mg |
| Lactose | 42 mg |
| Total | 200 mg |

What is claimed is:

1. A 3,4-dihydrocarbostyril derivative represented by the formula (I)

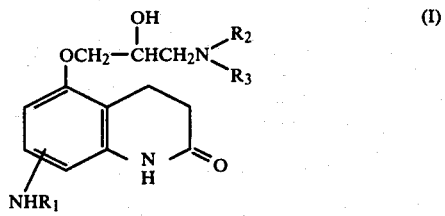

wherein $R_1$ represents an alkylcarbonyl group, a cycloakylcarbonyl group, an alkylsufonyl group, a phenylsulfonyl group, a carbamoyl group or an alkoxycarbonyl group, $R_2$ and $R_3$, which may be the same or different, each represents a hydrogen atom, an alkyl group, a phenylalkyl group or a phenoxyalkyl group, or $R_2$ and $R_3$ can form, when taken together with the nitrogen atom to which they are attached, a heterocyclic group selected from the group consisting of piperidono, pyrrolidino, morpholino and 1-piperazinyl which may be substituted with a phenyl group or an alkyl group having 1 to 4 carbon atoms, with the proviso that, when the group —$NHR_1$ is attached to the 8-position of the 3,4-dihydrocarbostyril nucleus in which $R_1$ represents an alkylcarbonyl group, and $R_2$ represents a hydrogen atom or an alkyl group, $R_3$ is a phenyl alkyl group or a phenoxy alkyl group, or $R_2$ and $R_3$ can form, when taken together with the nitrogen atom to which they are attached, said heterocyclic group, and the pharmaceutically acceptable acid addition salts thereof.

2. 8-Acetylamino-5-[3-(3,4-dimethoxyphenethylamino)-2-hydroxy]propoxy-3,4-dihydrocarbostyril, according to claim 1.

3. 8-Ureido-5-{3-[2-(4-methoxyphenoxy)ethylamino]-2-hydroxy}propoxy-3,4-dihydrocarbostyril, according to claim 1.

4. 8-Ethoxycarbonylamino-5-{3-[2-(4-carbamoylphenoxy)ethylamino]-2-hydroxy}propoxy-3,4-dihydrocarbostyril, according to claim 1.

5. 6-Acetylamino-5-[3-(3,4-dimethoxyphenethylamino)-2-hydroxy]propoxy-3,4-dihydrocarbostyril, according to claim 1.

6. 8-p-Toluenesulfonylamino-5-{3-[2-(4-carbamoylphenoxy)ethylamino]-2-hydroxy}propoxy-3,4-dihydrocarbostyril, according to claim 1.

7. 8-Ureido-5-[3-(4-m-chlorophenyl-1-piperazinyl)-2-hydroxy]propoxy-3,4-dihydrocarbostyril, according to claim 1.

* * * * *